(12) United States Patent
Metivier et al.

(10) Patent No.: US 9,187,414 B2
(45) Date of Patent: Nov. 17, 2015

(54) METHOD TO MANUFACTURE SURFACE ACTIVE COMPOUNDS SUCH AS SULFATE BETAINE

(71) Applicant: RHODIA OPERATIONS, Aubervilliers (FR)

(72) Inventors: Pascal Metivier, Shanghai (CN); Yan Zhao, Shanghai (CN); Zhaoyu Fan, Shanghai (CN)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 14/356,525

(22) PCT Filed: Nov. 6, 2012

(86) PCT No.: PCT/CN2012/084152
§ 371 (c)(1),
(2) Date: May 6, 2014

(87) PCT Pub. No.: WO2013/067915
PCT Pub. Date: May 16, 2013

(65) Prior Publication Data
US 2014/0343312 A1 Nov. 20, 2014

(30) Foreign Application Priority Data

Nov. 10, 2011 (WO) ................ PCT/CN2011/082033
Jun. 1, 2012 (WO) ................ PCT/CN2012/076403

(51) Int. Cl.
C07C 303/24 (2006.01)
C07C 305/10 (2006.01)

(52) U.S. Cl.
CPC ............. *C07C 303/24* (2013.01); *C07C 305/10* (2013.01)

(58) Field of Classification Search
CPC ............................ C07C 303/24; C07C 305/10
See application file for complete search history.

(56) References Cited

U.S. PATENT DOCUMENTS

| 4,824,867 A | 4/1989 | Smith et al. |
| 4,837,330 A | 6/1989 | Braun et al. |
| 4,855,423 A | 8/1989 | Braun et al. |
| 5,348,557 A | 9/1994 | Von Der Eltz et al. |

FOREIGN PATENT DOCUMENTS

| CA | 1312606 C | 1/1992 |
| CA | 2060079 A1 | 8/1992 |
| CN | 1087694 A | 6/1994 |
| JP | 63-104958 U | 7/1988 |
| JP | 63-243065 A | 10/1988 |
| WO | WO 2013067700 A1 | 5/2013 |

OTHER PUBLICATIONS

Hodgson et al. (J. Org. Chem. 2006, 71(22); 8510-8515).*
Kosaka, T., et al—"New Plant and New Applications of Sucrose Esters", 1976, Sucrochemistry: A Symposium Sponsored by the International Sugar Research Foundation, Inc., and by the Division of Carbohydrate Chemistry at the 172$^{nd}$ Meeting of the American Chemical Society, San Francisco, CA, Aug. 31-Sep. 2, 1976; Published—1977, John Hickson, Editor, vol. 41, American Chemical Society, pp. 84-96; 14 pgs.
James, Catherine E., et al—"Sucrose and Its Derivatives", 1989, Progress in the Chemistry of Organic Natural Products, vol. 55, pp. 117-184; 70 pgs.
Kunz, Markwart—Sucrose-based Hyrdophilic Building Blocks as Intermediates for the Synthesis of Surfactants and Polymers, 1991, Carbohydrates as Organic Raw Materials, Frieder Lichtenthaler, Editor, Developed from a Workshop Sponsored by Sudzucker AG, at the Technische Hochschule Darmstadt, Apr. 11-12, 1990, Weinheim-VCH, pp. 127-153; 29 pgs.
U.S. Appl. No. 14/356,512, Pascal Metivier, et al.

* cited by examiner

Primary Examiner — Valerie Rodriguez-Garcia
(74) Attorney, Agent, or Firm — Osha Liang LLP

(57) ABSTRACT

The present invention relates generally to novel methods of preparing compounds such as sulfate betaines by reacting an amine with a cyclic (poly)glycerol sulphate (CGS) compound and the compound such as sulfate betaine products obtained by using the same.

15 Claims, 2 Drawing Sheets

Fig.1

¹H NMR (CDCl₃)

Figure 2

METHOD TO MANUFACTURE SURFACE ACTIVE COMPOUNDS SUCH AS SULFATE BETAINE

CROSS-REFERENCE TO RELATED APPLICATIONS

This application is a U.S. national stage entry under 35 U.S.C. §371 of International Application No. PCT/CN2012/084152 filed Nov. 6, 2012, which claims priority to International Application No. PCT/CN2011/082033 filed on Nov. 10, 2011 and International Application No. PCT/CN2012/076403 filed on Jun. 1, 2012, the whole content of these applications being herein incorporated by reference for all purposes.

FIELD OF THE INVENTION

The present invention relates generally to a novel method of preparing a compound such as a sulfate betaine by reacting an amine with a cyclic (poly)glycerol sulphate (CGS) compound and the compound such as sulfate betaine products obtained by using the same.

BACKGROUND OF THE INVENTION

Sulfate betaines are a new type of betaines and show better performance than sulfonic betaine as surfactants.

Most of the surfactants produced by the chemical industry are based on petrochemicals. Many conventional surfactants containing 1,4-dioxane may be carcinogenic to humans. A number of efforts to use carbohydrates as bulk raw materials for synthesis of non-ionic surfactants have been reported. See Kosaka, T; Yamada T. in *Sucrochemistry ACS Symposium Series*, No. 41; John L. Hickson, Ed.; Am. Chem. Soc.: Washington, D.C., 1977, p 84; James, C. E.; Hough, L.; Khan, R. *Prog. Chem. Org. Natl. Products* 1989, 55, 117; and Kunz, M. in *Carbohydrates as Organic Raw Materials*. F. W. Lichtenthaler, Ed.; VCH: Weinheim, 1991, p 127. There has been a rapidly increasing demand for green surfactants, especially for sulfate betaines.

Till to now, several methods have been reported to synthesize sulfate betaines.

German patent application publication No. 1906851 discloses a method of synthesizing sulfate betaines. In the reaction, a tertiary amine was reacted with sulfur trioxide firstly and then reacted with ethylene oxide to obtain sulfate betaine as shown below:

Canada patent application publication No. 2060079 and patent No. 1312606, and Japan patent application publication Nos. 63243065 and 19870259848 describe reactions of preparing sulfate betaines by reacting an adduct of a base having a tertiary N atom and sulfur trioxide/sulphuric acid in the presence of an alkylene carbonate as a solvent as shown below:

U.S. Pat. Nos. 4,824,867 and 4,824,867 disclose a reaction in which a tertiary amine was reacted with chlorine alcohol, and then reacted with $SO_3/ClSO_3H$ to obtain the sulfate betaine as shown below:

Despite these attempts, there still remains a need to find novel and improved methods to synthesize compounds such as sulfate betaines for easy industrialization.

SUMMARY OF THE INVENTION

The objective of the present invention is to provide a method of preparing a surface active compound such as sulfate betaine by reacting an amine such as an amine as defined below with a cyclic (poly)glycerol sulphate (CGS) compound such as a CGS compound of formula (I) as defined below and the compound such as sulfate betaine products obtained by using the same.

One aspect of the current invention provides a method of preparing a compound such as sulfate betaine, comprising reacting an amine of formula (II)

wherein $R_1$, $R_2$ and $R_3$ are independently selected from H, C1-C32 alkyl, C2-C32 alkenyl, and C2-C32 alkynyl, wherein said alkyl, alkenyl and alkynyl groups optionally comprising one or more linkages selected from the group consisting of —NH—, —NH2, —N—, —OCO—, —COO—, —O—, —CONR4- and —NR4CO— wherein R4 is hydrogen or C1-C6 alkyl; $R_1$, $R_2$ and $R_3$ are not H at the same time;

with a CGS compound of formula (I):

wherein n is an integer from 0 to 20; and each —$C_3H_6O_2$— is independently a glycerol residual.

In some embodiments of the CGS compound of formula (I), each —$C_3H_6O_2$— is independently In some embodiments of the CGS compound of formula (I), n is 0 and the CGS compound of formula (I) is the compound of the following formula (I')

In some embodiments, the process of preparing a compound such as sulfate betaine is performed at a temperature of about 0-100° C., preferably from about room temperature to about 80° C., and most preferably 50-70° C.

In some embodiments, in the process of preparing a compound such as sulfate betaine, the amine and the CGS compound of formula (I) are used in a molar ratio of about 0.3:1 to 1.5:1.

Another aspect of the current invention provides a method of preparing a compound such as sulfate betaine, comprising steps of a) reacting a compound of formula (III) with an oxidant, for example a ruthenium-based oxidant system comprising a catalytic amount of a ruthenium compound and a second agent that oxidizes the ruthenium compound, to obtain the compound of formula (I) as described above, wherein n' is an integer from 0 to 20; and each —$C_3H_6O_2$— is independently a glycerol residual, and b) further reacting the resulting compound of formula (I) with an amine of formula (II)

according to the process of preparing a compound such as sulfate betaine as described above,
wherein $R_1$, $R_2$ and $R_3$ are independently selected from H, C1-C32 alkyl, C2-C32 alkenyl, and C2-C32 alkynyl, wherein said alkyl, alkenyl and alkynyl groups optionally comprising one or more linkages selected from the group consisting of —NH—, —NH2, —N—, —OCO—, —COO—, —O—, —CONR4- and —NR4CO— wherein R4 is hydrogen or C1-C6 alkyl; $R_1$, $R_2$ and $R_3$ are not H at the same time.

In some embodiments of the compound of formula (III), n' is 0 and the compound of formula (III) is the compound of the following formula (III')

In some embodiments, in the process of preparing a compound such as sulfate betaine as described above, the step a) and the step b) are performed in a manner of one-pot reaction.

Yet another aspect of the current invention provides a sulfate betaine of obtainable by the method of preparing a compound such as sulfate betaine as described above, wherein $R_1$, $R_2$ and $R_3$ are independently selected from C1-C32 alkyl, C2-C32 alkenyl, and C2-C32 alkynyl, wherein said alkyl, alkenyl and alkynyl groups optionally comprising one or more linkages selected from the group consisting of —NH—, —NH2, —N—, —OCO—, —COO—, —O—, —CONR4- and —NR4CO— wherein R4 is hydrogen or C1-C6 alkyl; and n is an integer from 0 to 20.

In some embodiments, the sulfate betaine is of the following formula wherein $R_1$, $R_2$ and $R_3$ are independently selected from C1-C32 alkyl, C2-C32 alkenyl, and C2-C32 alkynyl, wherein said alkyl, alkenyl and alkynyl groups optionally comprising one or more linkages selected from the group consisting of —NH—, —NH2, —N—, —OCO—, —COO—, —O—, —CONR4- and —NR4CO— wherein R4 is hydrogen or C1-C6 alkyl.

The compounds such as sulfate betaine according to the present invention can be used as surfactant in formulation for personal care as detergent, emulsifier, dispersant, foaming agent, moisturizer etc.

The methods described in the present invention show novel and improved processes for manufacturing compounds such as sulfate betaines. Furthermore, the compound such as sulfate betaines obtained by the methods of the present invention will produce new applications and better performance as compared with sulfonic betaines.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Unless otherwise stated, the following terms used in this application, including the specification and claims, have the definitions given below. It must be noted that, as used in the specification and the appended claims, the singular forms "a" "an" and "the" include plural referents unless the context clearly dictates otherwise. In this application, the use of "or" or "and" means "and/or" unless stated otherwise. Furthermore, use of the term "including" as well as other forms, such as "include", "includes" and "included" is not limiting.

In one aspect, the present invention provides methods of preparing a compound such as sulfate betaine by reacting an amine with a CGS compound. The method according to the present invention uses a novel reactant, i.e., cyclic glycerol sulphate which is glycerol-based. The present invention thereby provides a convenient way of producing compound such as sulfate betaine, which is suitable for manufacture of green products.

In a particular aspect, the present invention relates to a method of preparing a compound such as sulfate betaine, comprising reacting an amine of formula (II)

with a CGS compound of formula (I):

Preferably, in the amine of formula (II), $R_1$, $R_2$ and $R_3$ are independently hydrogen, alkyl, alkenyl or alkynyl, wherein the alkyl, alkenyl and alkynyl groups optionally comprise one or more linkages selected from the group consisting of —NH—, —NH2, —N—, —OCO—, —COO—, —O—, —CONR4- and —NR4CO— wherein R4 is hydrogen or C1-C6 alkyl.

Preferably, in the amine of formula (II), $R_1$, $R_2$ and $R_3$ are independently hydrogen, C1-C32 alkyl, C2-C32 alkenyl or C2-C32 alkynyl, wherein the alkyl, alkenyl and alkynyl groups optionally comprise one or more linkages selected from the group consisting of —NH—, —NH2, —N—, —OCO—, —COO—, —O—, —CONR4- and —NR4CO— wherein R4 is hydrogen or C1-C6 alkyl.

Preferably, in the amine of formula (II), one or two of R1, R2 and R3 are independently C7-32 alkyl, C7-32 alkenyl or C7-32 alkynyl; more preferably C8-30 alkyl, C8-30 alkenyl or C8-30 alkynyl; even more preferably, C12-26 alkyl, C12-C26 alkenyl or C12-C26 alkynyl; still more preferably C12-C24 alkyl, C12-C24 alkenyl or C12-C24 alkynyl; and the other R1, R2 and R3 group or groups are independently hydrogen or C1-6 alkyl, C2-C6 alkenyl or C2-6 alkynyl, more preferably H, CH3-, CH3CH2-, —CH$_2$CH$_2$OH or benzyl.

Whenever it appears herein, a numerical range such as "2 to 32" refers to each integer in the given range; e.g., an alkyl having "2 to 32 carbon atoms" (i.e. C2-C32 alkyl) means that the alkyl group comprises 2 carbon atoms, 3 carbon atoms, etc., up to and including 32 carbon atoms. The number of carbon atoms as specified in "C1-C32 alkyl", "C2-C32 alkenyl" and "C2-C32 alkynyl" does not include the carbon atoms contained in the one or more linkages (selected from the group consisting of —NH—, —NH2, —N—, —OCO—, —COO—, —O—, —CONR4- and —NR4CO— wherein R4 is hydrogen or C1-C6alkyl) that the alkyl, alkenyl and alkynyl groups optionally comprise. Similarly, the number of carbon atoms as specified in "C1-C32 alkyl", "C2-C32 alkenyl" and "C2-C32 alkynyl" does not include the carbon atoms contained in the one or more substituents (as explained below) that the alkyl, alkenyl and alkynyl groups optionally carries.

As used herein, the term of "alkyl" refers to a saturated aliphatic hydrocarbon group (which means that it does not contain any units of unsaturation, e.g. carbon-carbon double bonds or carbon-carbon triple bonds). The alkyl moiety may be branched, straight chain, or include a cyclic portion. The point of attachment of an alkyl is at a carbon atom that is not part of a ring. The "alkyl" moiety may have 1 to 40 carbon atoms. An alkyl can be a lower alkyl having e.g., 1-6 carbon atoms such as methyl, ethyl propanyl, butyl, pentyl, or hexyl. An akyl can also be a higher alkyl having 7-32 carbon atoms, for example 7, 8, 9, 10, 11, 12, 13, 14, 15, 16, 17, 18, 19, 20, 21, 22, 23, 24, 25, 26, 27, 28, 29, 30, 31 or 32 carbon atoms. Optionally, an alkyl, especially a higher alkyl, may comprise one or more (for example 1, 2 or 3) linkages selected from the group consisting of —NH—, —NH2, —N—, —OCO—, —COO—, —O—, —CONR4- and —NR4CO— wherein R4 is hydrogen or C1-C6 alkyl. An alkyl may optionally be substituted with one or more substituents such as those independently selected from the group consisting of hydroxyl, halogen, cyano, amino, nitro, oxo, acyl, aryl, heteroaryl, alkoxy, alkenyloxy, alkynyloxy, aryloxy, alkylthio, alkenylthio, alkynylthio, alkylamino, alkenylamino, alkynylamino, and acylamino.

As used herein, "alkenyl" groups are straight chain, branch chain, and cyclic hydrocarbon groups containing at least one carbon-carbon double bond. Alkenyl groups can be substituted. The "alkenyl" moiety may have 2 to 40 carbon atoms. An alkenyl can be a lower alkenyl having e.g., 2-6 carbon atoms such as ethenyl propenyl, butenyl, pentenyl, or hexenyl. An akenyl can also be a higher alkenyl having 7-32 carbon atoms, for example 7, 8, 9, 10, 11, 12, 13, 14, 15, 16, 17, 18, 19, 20, 21, 22, 23, 24, 25, 26, 27, 28, 29, 30, 31 or 32 carbon atoms. Optionally, an alkenyl, especially a higher alkenyl, may comprise one or more (for example 1, 2 or 3) linkages selected from the group consisting of —NH—, —NH2, —N—, —COO—, —O—, —CONR4- and —NR4CO— wherein R4 is hydrogen or C1-C6 alkyl. An alkenyl may optionally be substituted with one or more substituents such as those independently selected from the group consisting of hydroxyl, halogen, cyano, amino, nitro, oxo, acyl, aryl, heteroaryl, alkoxy, alkenyloxy, alkynyloxy, aryloxy, alkylthio, alkenylthio, alkynylthio, alkylamino, alkenylamino, alkynylamino, and acylamino.

As used herein, "alkynyl" groups are straight chain, branch chain, and cyclic hydrocarbon groups containing at least one carbon-carbon triple bond. The "alkynyl" moiety may have 1 to 40 carbon atoms. An alkynyl can be a lower alkenyl having e.g., 2-6 carbon atoms such as ethynyl propynyl, butyryl, pentynyl, or hexynyl. An akynyl can also be a higher alkynyl having 7-32 carbon atoms, for example 7, 8, 9, 10, 11, 12, 13, 14, 15, 16, 17, 18, 19, 20, 21, 22, 23, 24, 25, 26, 27, 28, 29, 30, 31 or 32 carbon atoms. Optionally, an alkynyl, especially a higher alkynyl, may comprise one or more (for example 1, 2 or 3) linkages selected from the group consisting of —NH—, —NH2, —N—, —OCO—, —COO—, —O—, —CONR4- and —NR4CO— wherein R4 is hydrogen or C1-C6 alkyl. An alkynyl may optionally be substituted with one or more substituents such as those independently selected from the group consisting of hydroxyl, halogen, cyano, amino, nitro, oxo, acyl, aryl, heteroaryl, alkoxy, alkenyloxy, alkynyloxy, aryloxy, alkylthio, alkenylthio, alkynylthio, alkylamino, alkenylamino, alkynylamino, and acylamino.

As used herein, an "acyl" refers to an alkyl(C=O), aryl (C=O), or aralkyl(C=O) group. An acyl moiety can have an intervening moiety (Y) that is oxy, amino, or thio between the carbonyl and the hydrocarbon group. For example, an acyl group can be alkyl-Y—(C=O), aryl-Y—(C=O) or aralkyl-Y—(C=O).

As used herein, the term "aryl" refers to an aromatic ring wherein each of the atoms forming the ring is a carbon atom. Aryl rings are formed by five, six, seven, eight, nine, or more than nine carbon atoms. Aryl groups are a substituted or unsubstituted. In one aspect, an aryl is a phenyl or a naphthalenyl.

As used herein, "heteroaryl" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms.

As used herein, an "alkoxy" group refers to an alklyl group linked to oxygen i.e. (alkyl)-O— group, where alkyl is as defined herein. Examples include methoxy (—$OCH_3$) or ethoxy (—$OCH_2CH_3$) groups.

As used herein, an "alkenyloxy" group refers to an alkenyl group linked to oxygen i.e. (alkenyl)-O— group, where alkenyl is as defined herein.

As used herein, an "alkynyloxy" group refers to an alkynyl group linked to oxygen i.e. (alkynyl)-O— group, where alkynyl is as defined herein.

As used herein, an "aryloxy" group refers to to an aryl group linked to oxygen i.e. (aryl)-O-group, where the aryl is as defined herein. An example includes phenoxy ($OC_6H_5$).

As used herein, the term "alkylthio" refers to an alkyl group attached to a bridging sulfur atom i.e. (alkyl)-S— group, wherein alkyl is defined herein. For example, an alkylthio is a methylthio and the like.

As used herein, the term "alkenylthio" refers to an alkenyl group attached to a bridging sulfur atom i.e. (alkenyl)-S— group, wherein alkenyl is defined herein.

As used herein, the term "alkynylthio" refers to an alkynyl group attached to a bridging sulfur atom i.e. (alkynyl)-S— group, wherein alkenyl is defined herein.

As used herein, the term "alkylamino" refers to an amino group substituted with at least one alkyl group i.e. —NH (alkyl) or —N-(alkyl)$_2$, wherein alkyl is defined herein.

As used herein, the term "alkenylamino" refers to an amino group substituted with at least one alkenyl group i.e. —NH (alkenyl) or —N-(alkenyl)$_2$, wherein alkenyl is defined herein.

As used herein, the term "alkynylamino" refers to an amino group substituted with at least one alkynyl group i.e. —NH (alkynyl) or —N-(alkynyl)$_2$, wherein alkynyl is defined herein.

As used herein, the term "oxo" refers to the structure of "=O".

As used herein, the term "halogen" is intended to include fluorine, chlorine, bromine and iodine.

As used herein, the term "acylamino" refers to the group RC(O)NH— where each R is alkyl, alkenyl, alkynyl as defined herein.

In some embodiments, the suitable examples of the amine include N,N-dimethyldodecan-1-amine, N-(3-(dimethylamino)propyl)dodecanamide, N-(3-dimethylamino)propyl) lauramide, dodecan-1-amine, N-(2-dimethylamino)ethyl) lauramide, and N-(3-(dimethylamino)propyl)oleic acid amide. Further examples of the amine are cetyldimethylamine, behenyldimethylamine, trimethylamine, triethylaime, stearylmethylbenzylamine, cocodimethylamine, PEG-2-oleamine, and ethylenediamine. Where at least one of R1, R2 or R3 contains a linkage of —CONR4- and —NR4CO— wherein R4 is hydrogen or C1-C6 alkyl, the amines of formula (II) will be amidoamines. Preferred amidoamines useful therein as the amines of formula (II) include stearamidopropyldimethylamine, stearamidopropyldiethylamine, stearamidoethyldimethylamine, stearamidoethyldiethylamine, palmitamidopropyldimethylamine, palmitamidopropyldiethylamine, palmitamidoethyldimethylamine, palmitamidoethyldiethylamine, behenamidopropyldimethylamine, behenamidopropyldiethylamine, behenamidoethyldimethylamine, behenamidoethyldiethylamine, arachidamidopropyldimethylamine, arachidamidopropyldiethylamine, arachidamidoethyldimethylamine, or arachidamidoethyldiethylamine.

According to the method of the present invention, in some embodiments of the CGS compound of formula (I), (I)

the number (n) of glycerol residual —$C_3H_6O_2$— can be any integer from 0 to 20, i.e., 0, 1, 2, 3, 4, 5, 6, 7, 8, 9, 10, 11, 12, 13, 14, 15, 16, 17, 18, 19 or 20. Preferably, n is an integer from 0 to 10, more preferably n is from 0 to 4, and most preferably n is 0.

In some embodiments of the CGS compound of formula (I), each of the glycerol residual —$C_3H_6O_2$— in formula (I) can be independently one of the following groups:

Therefore, the polyglycerol part of the CGS compound of Formula (I) can be a homopolymer of any one of the above —$C_3H_6O_2$— block or a copolymer of the two —$C_3H_6O_2$— blocks.

In a preferable embodiment of the CGS compound of formula (I), the present invention provides a compound of formula (I') (4-(hydroxymethyl)-1,3,2-dioxathiolane-2,2-dioxide):

(I')

The CGS compound of formula (I) and especially the CGS compound of formula (I') contains an asymmetrical center. It can exist as (S) enantiomer or (R) enantiomer or any mixture thereof. The present invention relates to any one of these different forms of the compound.

Interestingly, it has been found now that the compounds of formula (I), especially the compound of formula (I') are considerably stable in tetrahydrofuran (THF). Therefore, the present invention relates to a solution of a compound of formula (I) in THF. Particularly, the present invention relates to a solution of the compound of formula (I') in THF.

In an alternative embodiment, the compounds of formula (I) are prepared by reacting a compound of formula (III) with an oxidant, for example a ruthenium-based oxidant system comprising a catalytic amount of a ruthenium compound and a second agent that oxidizing the ruthenium compound, (III)

the number (n') of glycerol residual —$C_3H_6O_2$— can be any integer from 0 to 20, i.e., 0, 1, 2, 3, 4, 5, 6, 7, 8, 9, 10, 11, 12, 13, 14, 15, 16, 17, 18, 19 or 20. Preferably, n is an integer from 0 to 10, more preferably n is from 0 to 4, and most preferably n is 0. In addition to the ruthenium-based oxidant, other oxidant can be used in the preparation of the cyclic sulphates of formula (I) by the oxidation of corresponding sulfites of formula (III). Said other oxidants can be, for example, KMO4/H3O+, RuO4, Ca(MO4)2 or Ba(MnO4). Optionally, the free hydroxyl group(s) of the cyclic sulfites is/are protected before the oxidation and the protection group(s) is/are removed to free a hydroxyl group after the oxidation.

In some embodiments of the compound of formula (III), each of the glycerol residual —$C_3H_6O_2$— in formula (III) can be independently one of the following groups:

Therefore, the polyglycerol part of the compound of Formula (III) can also be a homopolymer of any one of the above —$C_3H_6O_2$— block or a copolymer of the two —$C_3H_6O_2$— blocks.

In a preferable aspect of the compound of formula (III), the compound of formula (III) is a compound of formula (III') (4-(hydroxymethyl)-1,3,2-dioxathiolane-2-oxide):

(III')

As used herein, the term "sulfite" relates to the structure of

As used herein, the term "sulphate" relates to the structure of

As used herein, the term "second agent" refers to an oxidant that can oxidize a ruthenium compound used in the reaction of the invention. Preferably, the second agent can oxidize the ruthenium compound used in the reaction.

The ruthenium-based oxidant system according to the present invention comprises, preferably essentially consisting of or consisting of, a catalytic amount of a ruthenium compound along with a second agent. It is believed that the ruthenium compound actually act as catalyst because it is re-oxidized by the second agent after the reaction with the substrate.

Preferably examples of the ruthenium compound according to the present invention are ruthenium dioxide, ruthenium trichloride and hydrate thereof, more preferably $RuCl_3 \cdot 3H_2O$.

Preferable examples of the second agent according to the present invention are periodate, permanganate, hypochlorite, bromate, peracetic acid, periodic acid, oxygen, cerium sulfate, electrochemically generated Chlorine, and monoperoxysulfate. More preferably, the second agent according to the present invention is selected from the group comprising periodate, permanganate, hypochlorite, more preferably $NaIO_4$, $KMnO_4$, $NaClO$, and the mixture thereof.

Since ruthenium compound can be produced repeatedly when the oxidant system of the inventions is working, a catalytic amount of ruthenium compound is sufficient to complete the reaction of the present invention. Ruthenium compounds are generally expensive reagents and it is advantageously to use as less these reagents as possible. Preferably, the said ruthenium compound and said second agent are used in the mole ratio of 1:10-1:500, more preferably 1:50-1:300, most preferably 1:100. Preferably, the molar ratio of the cyclic sulfite of formula (III) and the ruthenium compound is about 1:0.0001 to 1:0.01; more preferably about 1:0.001 to 1:0.005.

Thus, in another aspect, the present invention provides a method of preparing compound such as sulfate betaine, comprising steps of
a) reacting a compound of formula (III) with an oxidant such as a ruthenium-based oxidant system comprising a catalytic amount of a ruthenium compound and a second agent that oxidizes the ruthenium compound, as described above, to obtain the compound of formula (I), and
b) further reacting the resulting compound of formula (I) with an amine of wherein $R_1$, $R_2$ and $R_3$ are defined as above.

In some embodiments, the step a) and the step b) are performed in a manner of one-pot reaction. As used herein, "one-pot reaction" means a chemical reaction wherein a reactant is subjected to successive chemical reactions in just one reactor.

According to the present invention, the process of reacting an amine with the compound of formula (I), the process of preparing the compound of formula (I) from the compound of formula (III) and the one-pot reaction, as described above, are carried out at a suitable temperature that can be determined by those skilled in the art, for example a temperature of about 0-100° C., preferably from about room temperature (e.g., 20° C.) to about 80° C. and most preferably about 50-70° C. Exemplary temperature of the reaction is about 20° C., 25° C., 30° C., 35° C., 40° C., 45° C., 50° C., 55° C., 60° C., 65° C., or 70° C.

The ratio of each reactant in the process of the present invention can be determined by those skilled in the art. For example, in the process of preparing compound such as sulfate betaine, the amine and the CGS compound of formula (I) are used in a molar ratio of about 0.3:1 to 1.5:1, such as 0:3:1, 0.4:1, 0.5:1, 0.6:1, 0.7:1, 0.8:1, 0.9:1, 1.0:1, 1.1:1, 1.2:1, 1.3:1, 1.4:1 and 1.5:1. Yet for example, in the process of preparing the compound of formula (I) from the compound of formula (III), the ruthenium compound and the second agent are used in the mole ratio of 1:10-1:500, more preferably 1:50-1:300, most preferably 1:100.

The compounds such as sulfate betaines obtained by using the methods of the present invention can be characterized by any conventional analytical means, such as $^1$H-NMR, $^{13}$C NMR, HPLC, MS and the like.

The surfactants of sulfate betaines prepared by using the method of the present invention do not contain any 1,4-dioxane. The CGS compound of formula (I) containing free hydroxyl group would be a very important intermediate in the preparation of the green surfactants of sulfate betaines.

In another aspect, the present invention provides sulfate betaines having the general formula of wherein $R_1$, $R_2$ and $R_3$ are define as above. The number (n) of glycerol residual —$C_3H_6O_2$— can be any integer from 0 to 20, i.e., 0, 1, 2, 3, 4, 5, 6, 7, 8, 9, 10, 11, 12, 13, 14, 15, 16, 17, 18, 19 or 20. Preferably, n is an integer from 0 to 10, more preferably n is from 0 to 4, and most preferably n is 0. In some embodiments, each of the glycerol residual —$C_3H_6O_2$— can be independently one of the following groups:

The polyglycerol part can be a homopolymer of any one of the above —$C_3H_6O_2$— block or a copolymer of the two —$C_3H_6O_2$— blocks.

In some embodiments, the sulfate betaines described above have the general formula of wherein $R_1$, $R_2$ and $R_3$ are defined as above.

In a preferred embodiment, the sulfate betaine of the present invention is the following compound:

The invention also concerns a compound of the following formula:

wherein $R_1$, $R_2$ are independently selected from H, C1-C32 alkyl, C2-C32 alkenyl, and C2-C32 alkynyl, wherein said alkyl, alkenyl and alkynyl groups optionally comprising one or more linkages selected from the group consisting of —NH—, —NH2, —N—, —OCO—, —COO—, —O—, —CONR4- and —NR4CO— wherein R4 is hydrogen or C1-C6 alkyl; $R_1$, $R_2$ are not H at same time, wherein n is an integer from 0 to 20; and each —$C_3H_6O_2$— is independently a glycerol residual.

The invention also concerns a compound of the following formula:

wherein $R_1$ are selected from H, C1-C32 alkyl, C2-C32 alkenyl, and C2-C32 alkynyl, wherein said alkyl, alkenyl and alkynyl groups optionally comprising one or more linkages selected from the group consisting of —NH—, —NH2, —N—, —OCO—, —COO—, —O—, —CONR4- and —NR4CO— wherein R4 is hydrogen or C1-C6 alkyl; wherein n is an integer from 0 to 20; and each —$C_3H_6O_2$— is independently a glycerol residual The invention also concerns the use of these compounds as surfactants in formulation for personal care products. These compounds may serve as detergent, emulsifier, dispersant, foaming agent or moisturizer.

These types of compounds such as sulfate betaines are amphoteric surfactants which have both anionic and cationic groups, allowing them to be soluble at acid, alkaline and neutral medium. By using the CGS compound of formula (I) to synthesize said sulfate betaines, one would not only be able to prepare lots of useful and important sulfate betaines, but also control the position of introducing the polyglycerol part specifically at alpha carbon next to sulfate.

The green surfactants of sulfate betaines obtained by using the method of the present invention can be used in many applications. For example, the surfactants of sulfate betaines can be used as pharmaceutical excipients such as a laxative in enemas, as an excipient on dissolvable caplets of, e.g., aspirins and other fiber therapy. The surfactants of sulfate betaines may also be used in detergents, fabric softeners, emulsions, paints, adhesives, inks, anti-fogs, ski waxes, snowboard wax, deinking of recycled papers, washing and enzymatic processes, laxatives, agrochemical formulations, quantum dot coatings, biocides (sanitizers), cosmetics including shampoos, hair conditioners (after shampoo) and toothpastes.

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. All such similar substitutes and modifications apparent to those skilled in the art are deemed to be within the spirit, scope and concept of the invention as defined by the appended claims.

Example 1

Synthesis of CGS (4-(hydroxymethyl)-1,3,2-dioxathiolane-2,2-dioxide)

A 250 ml three-necked round-bottom flask was charged with 6.9 g cyclic glycerol sulfite (4-(hydroxymethyl)-1,3,2-dioxathiolane-2-oxide), 50 ml acetonitrile, 100 mg $RuCl_3 \cdot 3H_2O$ and 16 g $NaIO_4$, the mixture was cooled down to 0-5° C. by ice-salt bath. Then 75 ml cooled water was added into the mixture, the temperature increased to 30° C., the mixture stirred for 5 mins, the mixture became green suspension. 400 ml ethyl acetate and 40 ml saturated $NaHCO_3$ solution was added into the mixture. The mixture was separated to two phases. The water phase was extracted by ethyl acetate (100 ml×2). The combined organic phase was washed by 40 ml water and dried by anhydrous $Na_2SO_4$. The solvent was removed with a rotary evaporator to yield 5.6 g yellow liquid desired product, crude yield: 72.7%.

Figure 1:
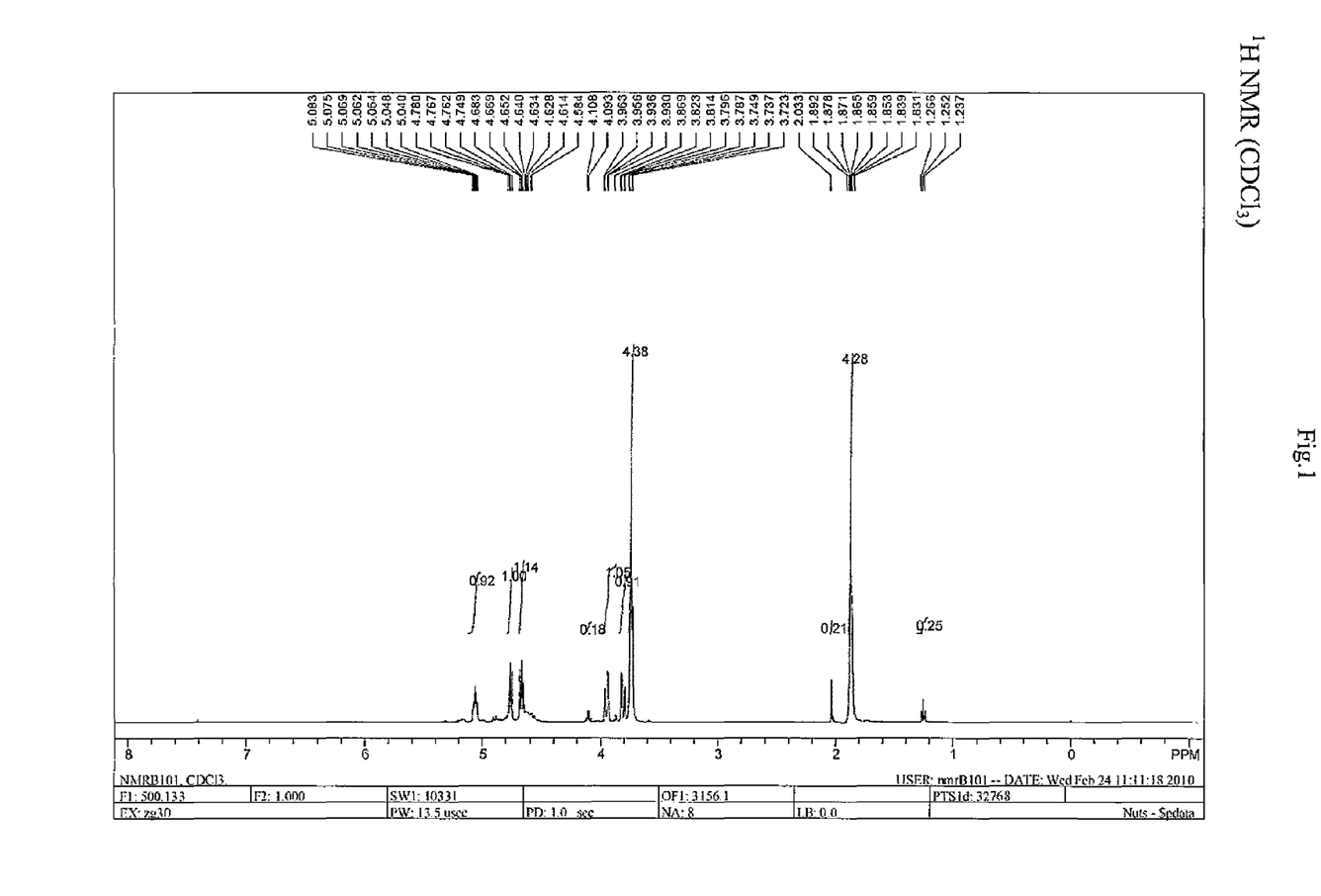
FIG. 1 is the $^1$H NMR (CDCl$_3$) spectrum of CGS

$^1$H NMR ($CDCl_3$, 500 MHz), δ: 5.05-5.08 (m, 1H), 4.75-4.78 (m, 1H), 4.63-4.68 (m, 1H), 3.95-3.96 (m, 1H), 3.80-3.82 (m, 1H) as shown in FIG. 1.

Example 2

7.64 g of N,N-dimethyldodecan-1-amine and 25 ml of THF were charged into a 50 ml of three-necked round-bottomed flask, 5.36 g of CGS as obtained from Example 1 (in 10 ml of THF) was added dropwise into it in about 10 mins, then it was heated with an oil bath to reflux and stirred for sometime, many bubbles in the bottom, followed with $^1$H-NMR, then it was cooled to room temperature and filtered, washed with THF, dried, 7.9 g of white solid was obtained as shown below.

Figure 2:
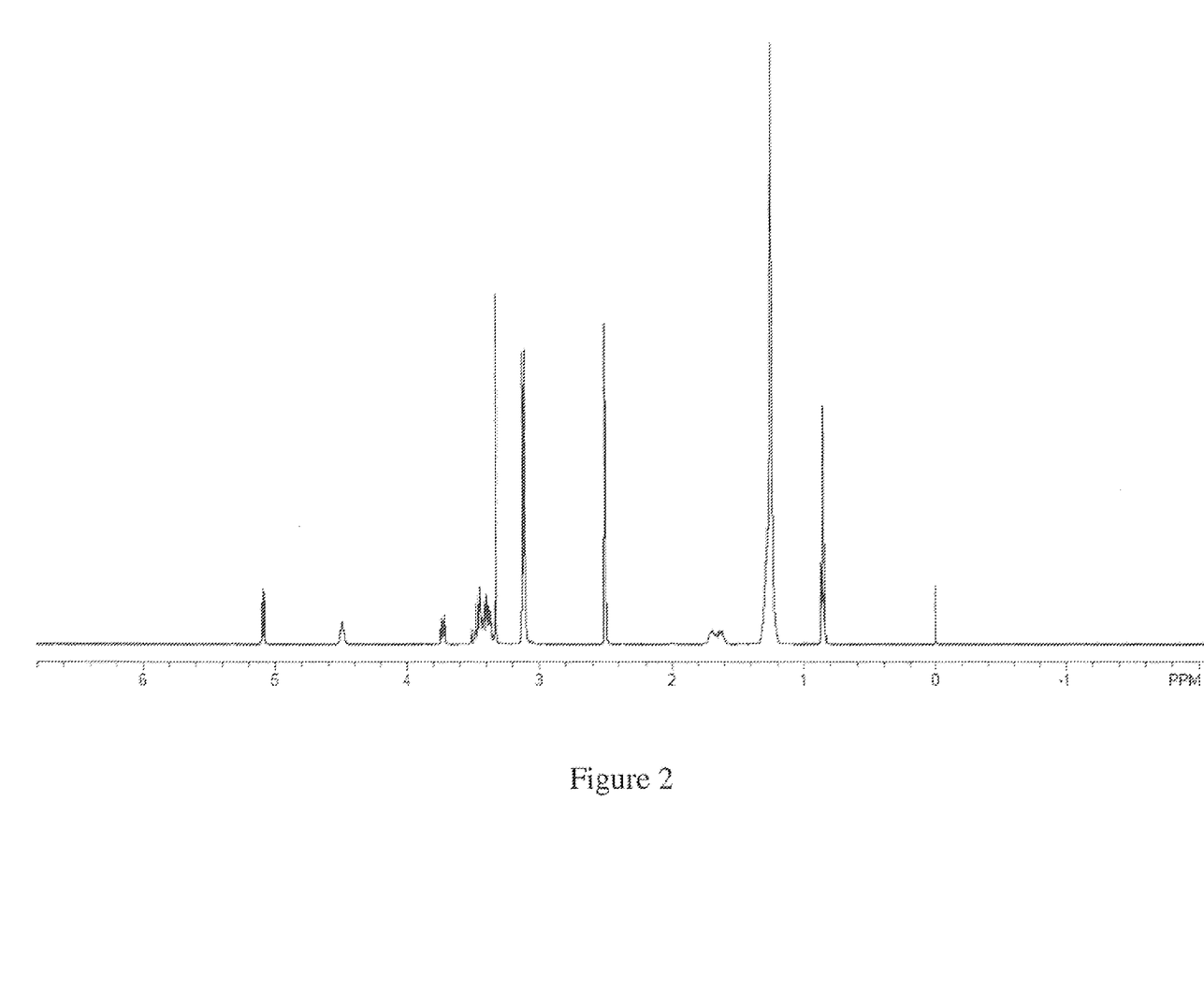
FIG. 2 is the $^1$H-NMR (CDCl$_3$) spectrum of the sulfate betaine obtained in Example 2.

$^1$H-NMR (CDCl$_3$, 500 MHz) is shown as in FIG. 2.

Example 3

9.6 g N-(3-(dimethylamino)propyl)dodecanamide and 25 ml of THF were charged into a 50 ml of three-necked round-bottomed flask, 5.36 g of CGS as obtained from Example 1 (in 10 ml of THF) was added dropwise into it in about 10 mins, then it was heated with an oil bath to reflux and stirred for sometime, many bubbles in the bottom, followed with $^1$H-NMR, then it was cooled to room temperature and filtered, washed with THF, dried, of white solid was obtained.

$^1$H NMR (D_DMSO, 300 MHz), δ: 7.84-7.81 (m, 1H), 5.11-5.07 (m, 1H), 4.53-4.52 (m, 1H), 3.75-3.69 (m, 1H), 3.50-3.41 (m, 6H), 3.13-3.08 (m, 8H), 2.08-2.03 (t, 2H), 1.83-1.82 (m, 2H), 1.50-1.45 (m, 2H), 1.25-1.23 (m, 16H), 0.89-0.87 (t, 3H)

Example 4

9.6 g N-(3-(dimethylamino)propyl)lauramide and 25 ml of THF were charged into a 50 ml of three-necked round-bottomed flask, 5.36 g of CGS as obtained in Example 1 (in 10 ml of THF) was added dropwise into it in about 10 mins, it rose to 30° C., then it was heated with an oil bath to reflux and stirred for sometime, many bubbles in the bottom, followed with $^1$H-NMR, then it was cooled to room temperature and filtered, washed with THF, dried, of white solid was obtained.

$^1$H NMR (D_DMSO, 300 MHz), δ: 7.84-7.81 (m, 1H), 5.11-5.07 (m, 1H), 4.53-4.52 (m, 1H), 3.75-3.69 (m, 1H), 3.50-3.41 (m, 6H), 3.13-3.08 (m, 8H), 2.08-2.03 (t, 2H), 1.83-1.82 (m, 2H), 1.50-1.45 (m, 2H), 1.25-1.23 (m, 16H), 0.89-0.87 (t, 3H)

Example 5

6.29 g of dodecan-1-amine and 25 ml of THF were charged into a 50 ml of three-necked round-bottomed flask, 5.36 g of CGS as obtained in Example 1 (in 10 ml of THF) was added dropwise into it in about 10 mins, then it was heated with an oil bath to reflux and stirred for sometime, then 50% NaOH was added to adjust the pH to 7-8, about 1 hour later, lots of solid was separated out, followed with $^1$H-NMR, then it was cooled to room temperature and filtered, washed with THF, dried, 7.8 g of white solid was obtained, yield 64%.

$^1$H NMR (D$_2$O, 500 MHz), δ: 4.43-4.41 (m, 1H), 3.71-3.65 (m, 2H), 2.77-2.67 (m, 2H), 2.53-2.51 (m, 2H), 1.45-1.43 (m, 2H), 1.21-1.22 (m, 18H), 0.79 (t, 3H)

Example 6

6.76 g of N-methyldodecan-1-amine and 25 ml of THF were charged into a 50 ml of three-necked round-bottomed flask, 5.36 g of CGS as obtained in Example 1 (in 10 ml of THF) was added dropwise into it in about 10 mins, then it was heated with an oil bath to reflux and stirred for sometime, then 50% NaOH was added to adjust the pH to 7-8, about 1 hour later, lots of solid was separated out, followed with $^1$H-NMR, then it was cooled to room temperature and filtered, washed with THF, dried, 12.75 g of white solid was obtained, yield 100%.

$^1$H NMR (DMSO, 500 MHz), δ: 4.56 (s, 1H), 4.45-4.42 (m, 1H), 3.67-3.65 (m, 1H), 3.48-3.46 (m, 1H), 3.34-3.10 (m, 4H), 2.85 (s, 3H), 1.60 (m, 2H), 1.24-1.26 (m, 18H), 0.86 (t, 3H)

Example 7

9.5 g N-(2-(dimethylamino)ethyl)Lauramide and 25 ml of THF were charged into a 50 ml of three-necked round-bottomed flask, 5.36 g of CGS as obtained in Example 1 (in 10 ml of THF) was added dropwise into it in about 10 mins, then it was heated with an oil bath to reflux and stirred for sometime, many bubbles in the bottom, followed with $^1$H-NMR, then it was cooled to room temperature and filtered, washed with THF, dried, of white solid was obtained.

Example 8

9 g of oleic amine and 25 ml of THF were charged into a 50 ml of three-necked round-bottomed flask, 5.36 g of CGS as obtained in Example 1 (in 10 ml of THF) was added dropwise into it in about 10 mins, then it was heated with an oil bath to reflux and stirred for sometime, many bubbles in the bottom, followed with $^1$H-NMR, then it was cooled to room temperature and filtered, washed with THF, dried, white solid was obtained.

$^1$H NMR (D-DMSO, 500 MHz), δ: 4.15-4.12 (m, 1H), 3.60-3.40 (m, 3H), 2.71-2.69 (m, 1H), 2.58-2.50 (m, 2H), 1.40-1.30 (m, 2H), 1.24 (S, 13H), 0.86 (t, 3H)

Example 9

One eq. of oleic acid was reacted with 1 ep. NH$_2$(CH$_2$)$_3$N(CH$_3$)$_2$ to obtain amide, and then add into 25 ml of THF, charged into a 50 ml of three-necked round-bottomed flask, 1 eq of CGS as obtained in Example 1 (in 10 ml of THF) was added dropwise into it in about 10 mins, then it was heated with an oil bath to reflux and stirred for sometime, many bubbles in the bottom, followed with $^1$H-NMR, then it was cooled to room temperature and filtered, washed with THF, dried, white solid was obtained.

$^1$H NMR (DMSO, 500 MHz), δ: 7.91-7.85 (m, 1H), 5.33-5.31 (m, 2H), 4.52-4.51 (m, 1H), 3.74-3.70 (m, 1H), 3.50-3.35 (m, 5H), 3.13-3.06 (m, 8H), 2.07-2.03 (m, 2H), 2.00-1.95 (m, 4H), 1.83-1.80 (m, 2H), 1.49-1.45 (m, 2H), 1.24-1.28 (m, 20H), 0.85 (t, 3H)

Example 10

A 250 ml three-necked round-bottom flask was charged with 6.9 g cyclic glycerol sulfite (4-(hydroxymethyl)-1,3,2-dioxathiolane-2-oxide), 50 ml THF, 100 mg RuCl$_3$.3H$_2$O and 16 g NaIO$_4$, the mixture was cooled down to 0-5° C. by ice-salt bath. Then 75 ml cooled water was added into the mixture, the temperature increased to 30° C., the mixture stirred for 5 mins, the mixture became green suspension. 7.64 g of N,N-dimethyldodecan-1-amine in 25 ml of THF were charged into the three-necked round-bottomed flask dropwise in about 10 mins, then it was heated with an oil bath to reflux and stirred for sometime, many bubbles in the bottom, followed with $^1$H-NMR, then it was cooled to room temperature and filtered, washed with THF, dried, 8.3 g of white solid was obtained.

$^1$H-NMR (CDCl$_3$, 500 MHz) is same with example 2.

Example 11

To a 500 ml of three-necked round-bottomed flask charged with C12-CGS (40 g 124.04 mmol 1 eq) and 200 ml THF, ethylenediamine (11.18 g 186.06 mmol 1.5 eq) dissolved in 50 ml THF was added, the temperature climbed to 50° C., and then the reaction mixture was stirred overnight at r.t, and the reaction mixture was monitored by LC-MS. The reaction was filtrated, and the filtrate-cake was dried and 20 g white solid was obtained. The 20 g white solid was added into 150 ml THF and 20 ml MeOH, heated to reflux and stirred for 3 hrs, and then cooled to r.t, filtrated and dried, 18.5 g pure product was obtained, purity 98.52% (ELSD), yield 38.99%.

$^1$H NMR (D-DMSO, 300 MHz), δ: 4.24-4.19 (m, 1H), 3.53-3.49 (m, 2H), 3/39-3.34 (m, 4H), 2.81-2.59 (m, 6H), 1.47-1.45 (m, 2H), 1.24 (S, 18H), 0.89-0.83 (t, 3H)

Example 12

A 250 ml three-necked round-bottom flask was charged with 13.8 g cyclic glycerol sulfite (4-(hydroxymethyl)-1,3,2-dioxathiolane-2-oxide), 100 ml THF, 200 mg RuCl$_3$.3H$_2$O and 32 g NaIO$_4$, the mixture was cooled down to 0-5° C. by ice-salt bath. Then 150 ml cooled water was added into the mixture, the temperature increased to 30° C., the mixture stirred for 5 mins, the mixture became green suspension. 9.25 g of dodecan-1-amine in 25 ml of THF were charged into the three-necked round-bottomed flask dropwise in about 10 mins, then it was heated with an oil bath to reflux and stirred for some time, then 50% NaOH was added to adjust the pH to 7-8, about 1 hour later, lots of solid was separated out, followed with $^1$H-NMR, then it was cooled to room temperature and filtered, washed with THF, dried, 2.7 g of white solid was obtained, yield 29%.

What is claimed is:

1. A method of preparing a sulfate betaine of formula (IV)

wherein R$_1$, R$_2$ and R$_3$ are defined below, comprising reacting an amine of formula (II)

wherein R$_1$, R$_2$ and R$_3$ are independently selected from the group consisting of H, C1-C32 alkyl, C2-C32 alkenyl, and C2-C32 alkynyl, wherein said alkyl, alkenyl and alkynyl groups are optionally interrupted with one or more linkages selected from the group consisting of —NH—, —N—, —OCO—, —COO—, —O—, —CONR4- and —NR4CO— and are optionally substituted with one or more substituents independently selected from the group consisting of hydroxyl, halogen, cyano, amino, nitro, oxo, acyl, aryl, heteroaryl, alkoxy, alkenyloxy, alkynyloxy, aryloxy, alkylthio, alkenylthio, alkynylthio, alkylamino, alkenylamino, alkynylamino, and acylamino, wherein R4 is hydrogen or C1-C6 alkyl; and R$_1$, R$_2$ and R$_3$ are not H at the same time;

with a cyclic (poly)glycerol sulphate compound of formula (I):

wherein n is an integer from 0 to 20; and each —C$_3$H$_6$O$_2$— is independently a glycerol residual.

2. The method according to claim 1, wherein each —C$_3$H$_6$O$_2$— is independently 3. The method according to claim 1, wherein n is 0 and the compound of formula (I) is the compound of the following formula (I')

(I')

4. The method according to claim 1, wherein, in the amine of formula (II), one or two of R1, R2 and R3 are independently C7-32 alkyl, C7-32 alkenyl or C7-32 alkynyl; and the other R1, R2 and R3 group or groups are independently hydrogen, C1-6 alkyl, C2-C6 alkenyl or C2-6 alkynyl.

5. The method according to claim 1, wherein the reaction is performed at a temperature of about 0-100° C.

6. The method according to claim 1, wherein the amine and the cyclic (poly)glycerol sulphate are used in a molar ratio of about 0.3:1 to 1.5:1.

7. A method of preparing a sulfate betaine of formula (IV) as defined in claim 1, comprising the steps of
a) reacting a compound of formula (III) below with an oxidant to obtain the compound of formula (I) of claim 1, (III)

wherein n' is an integer from 0 to 20; and each —$C_3H_6O_2$— is independently a glycerol residual, and
b) further reacting the resulting compound of formula (I) of claim 1 with an amine of formula (II)

according to the method of claim 1,
wherein $R_1$, $R_2$ and $R_3$ are defined as claim 1.

8. The method according to claim 7, wherein said n' is 0 and the compound of said formula (III) is the compound of the following formula (III')

(III')

9. The method according to claim 7, wherein the amine is selected from amines of formula (II)

(II)

wherein in the amine of formula (II), one or two of R1, R2 and R3 are independently C7-32 alkyl, C7-32 alkenyl or C7-32 alkynyl; and the other R1, R2 and R3 group or groups are independently hydrogen, C1-6 alkyl, C2-C6 alkenyl or C2-6 alkynyl.

10. The method according to claim 7, wherein the step a) and the step b) are performed in a manner of one-pot reaction.

11. The method according to claim 1, wherein, in the amine of formula (II), one or two of R1, R2 and R3 are independently C8-30 alkyl, C8-30 alkenyl or C8-30 alkynyl; and the other R1, R2 and R3 group or groups are independently hydrogen, C1-6 alkyl, C2-C6 alkenyl or C2-6 alkynyl.

12. The method according to claim 1, wherein, in the amine of formula (II), one or two of R1, R2 and R3 are independently C12-26 alkyl, C12-C26 alkenyl or C12-C26 alkynyl; and the other R1, R2 and R3 group or groups are independently hydrogen, C1-6 alkyl, C2-C6 alkenyl or C2-6 alkynyl.

13. The method according to claim 1, wherein, in the amine of formula (II), one or two of R1, R2 and R3 are independently C12-C24 alkyl, C12-C24 alkenyl or C12-C24 alkynyl; and the other R1, R2 and R3 group or groups are independently hydrogen, C1-6 alkyl, C2-C6 alkenyl or C2-6 alkynyl.

14. The method according to claim 1, wherein, in the amine of formula (II), one or two of R1, R2 and R3 are independently C7-32 alkyl, C7-32 alkenyl or C7-32 alkynyl; and the other R1, R2 and R3 group or groups are independently H, CH3-, CH3CH2-, —$CH_2CH_2OH$ or benzyl.

15. The method according to claim 7, wherein the oxidant is a ruthenium-based oxidant system which comprises a catalytic amount of a ruthenium compound and a second agent that oxidizes the ruthenium compound.

* * * * *